United States Patent [19]

Hosoda

[11] Patent Number: 4,952,613
[45] Date of Patent: Aug. 28, 1990

[54] DENTAL COMPOSITIONS BASED ON ORGANIC CARBOXYLIC ACIDS/ANHYDRIDES, METAL CHLORIDES, AND WATER

[75] Inventor: Hiroyasu Hosoda, Tokyo, Japan

[73] Assignee: Kuraray Co., Ltd., Kurashiki, Japan

[21] Appl. No.: 252,053

[22] Filed: Sep. 30, 1988

[30] Foreign Application Priority Data

Sep. 30, 1987 [JP] Japan .................... 62-248631
Jan. 14, 1988 [JP] Japan .................... 63-6603

[51] Int. Cl.$^5$ .................... C08J 7/14; C08K 3/10; C08K 3/16; A61K 6/04
[52] U.S. Cl. .................... 523/109; 106/35; 424/49; 433/226; 433/228.1
[58] Field of Search .................... 106/35; 424/49; 433/226, 228.1; 523/109; 524/401

[56] References Cited

U.S. PATENT DOCUMENTS 4,535,102 8/1985 Kusumoto et al. ............ 433/228.1
4,659,751 4/1987 Bowen ............ 433/228.1

OTHER PUBLICATIONS

Kojima et al., Journal of the Japanese Society for Dental Materials and Devices, 1, 131, 1982.

Primary Examiner—John Kight, III
Assistant Examiner—Carlos Azpuru
Attorney, Agent, or Firm—Oblon, Spivak, McClelland, Maier & Neustadt

[57] ABSTRACT

A dental composition for the treatment of the enamel and/or dentin of the tooth comprising an organic carboxylic acid or an anhydride thereof, a metal chloride and water, the concentration of said organic carboxylic acid or anhydride thereof being 5 to 50 weight percent based on the total weight of said composition, said metal chloride being potassium chloride or calcium chloride or a mixture thereof and the concentration of said metal chloride being 5 to 50 weight percent based on the total weight of said composition. The composition assures an improved bond between the tooth and a filling material such as a composite resin, a pit and fissure sealant, a cementing agent or the like which is used in the treatment of caries, for instance.

5 Claims, No Drawings

DENTAL COMPOSITIONS BASED ON ORGANIC CARBOXYLIC ACIDS/ANHYDRIDES, METAL CHLORIDES, AND WATER

BACKGROUND OF THE INVENTION

1. Field of the Invention:

This invention relates to a dental treatment with a dental composition adapted to improve the bond between the tooth and a dental filling meterial. In a further aspect, the invention relates to a dental composition for assuring an improved bond between the tooth and a filling material such as a composite resin, a pit and fissure sealant, a cementing agent or the like which is used in the treatment of caries, for instance.

2. Description of the Related Art:

In the treatment of dental caries, it is common practice to pretreat the enamel of the affected tooth with an aqueous acid solution for assuring a firm bond between the tooth and an organic material (e.g. composite resin, glass ionomer cement, carboxylate cement, composite resin cement, and pit and fissure sealant). As such an enamel treating agent, an aqueous solution of phosphoric acid or citric acid has heretofore been employed widely and from the standpoint of effectiveness, an aqueous solution containing 20 to 60 percent by weight of phosphoric acid has been recommended.

The composite resin used in the restorative filling of the carious portion of a tooth, which consists of a synthetic resin and an inorganic filler, has only a poor adhesive ability for the tooth and much research has been undertaken for improving the adhering power. The effective restorative procedure heretofore known for dental caries comprises removing the carious part of the tooth, etching the enamel wall of the resulting cavity with an aqueous acid solution (e.g. an aqueous solution of phosphoric acid), then applying an adhesive containing a polymerizable monomer which is a component of a composite resin and finally filling the cavity with the composite resin. However, since the tooth comprises enamel and dentin and the cavity formed by removal of a carious portion has exposed walls of both enamel and dentin, it is desirable that the composite resin be able to firmly bond to both enamel and dentin. For this reason, the recent practice exploits adhesives containing a special polymerizable monomer having an affinity for dentin.

When the carious tooth is cut with burs, a smeared layer is formed on the cut surface. It is believed that this smeared layer includes the bacteria derived from the caries and those resident in the oral cavity. If a restorative procedure with a composite resin is performed with the smeared layer as it is, the composite resin will separate from the smeared layer because the smeared layer is brittle. Moreover, the irritating effect which the bacteria included in the smeared layer exerts on the dental pulp may also be a serious concern. Therefore, the smeared layer is preferably removed before the restorative procedure using a composite resin is actually undertaken.

If the whole surface of the burred cavity is treated with an aqueous solution of phosphoric acid, the smeared layer on the enamel and dentin will be completely removed but the dentinal tubules plugged by the smeared layer will then be exposed and irritant substances may easily reach the pulp through the tubules to cause undesirable effects. Therefore, attempts were made to use various organic carboxylic acids, in lieu of phosphoric acid, for the pretreatment of the dentin. It has been reported that the use of an aqueous solution of citric acid, oxalic acid or formic acid and/or a metal salt such as ferric oxalate, ferric chloride or the like was effective for the aforementioned purpose (e.g. Nakabayashi et al., Journal of the Japan Society for Dental Apparatus and Materials, 23, 61, 29–33, 1982). However, even when the enamel is pretreated with such a known agent, the bond between the composite resin and the enamel is not as good as that attainable by using an aqueous solution of phosphoric acid. Therefore, it is generally necessary to first pretreat the dentin with an organic carboxylic acid or the like and then pretreat the enamel with an aqueous solution of phosphoric acid, thus adding to the complexity of the restorative procedure.

Thus, while the dental treating agents containing oprganic carboxylic acids are effective for dentin, they are not so effective for enamel and, therefore, the enamel must be subsequently treated with an aqueous solution of phosporic acid, thus adding to the complexity of the clinical procedure as mentioned just above. Thus, organic carboxylic acids are not universally suited for the treatment of all classes of dental caries.

Although the most important function which a dental treating agent is expected to perform is an enhancement of the bond strength between the filling material and the enamel and dentin, it is also important that such an agent have little denaturation effect on the dentin, particularly on its collagen.

SUMMARY OF THE INVENTION

Accordingly, it is an object of the present invention to provide a dental composition for treatment of enamel or dentin of a tooth which is characterized by enhanced bond strenght and which causes very little denaturation of collagen or dentin.

It is yet another object of the present invention to provide a dental composition which is not based on phosphoric acid, and which simultaneously treats both the enamel and dentin of a tooth for successful restoration.

These and other objects of the present invention as will hereinafter become more readily apparent, have been atttained by the employment of an organic carboxylic acid which is acknowledged to be effective for the dentin without adverse effects on the pulp, in combination with an asdditive agent which will potentiate the adhering ability of the organic carboxylic acid on the enamel. This invention has been accomplished on the basis of the above research.

The dental composition provided by this invention comprises, as essential components, an organic carboxylic acid, a metal chloride, and water.

DETAILED DESCRIPTION OF THE PREFERRED EMBODIMENTS

The organic carboxylic acids useful for this invention include monocarboxylic acids, dicarboxylic acids, tricarboxylic acids, tetracarboxylic acids and anhydrides thereof.

As exemplary species of such monocarboxylic acids and anhydrides thereof, there may be mentioned formic acid, acetic acid, lactic acid, butyric acid, valeric acid, nonanoic acid, hexanoic acid, heptanoic acid, lauric acid, pyruvic acid, glycine, methacrylic acid, acrylic acid, crotonic acid, benzoic acid, aminobenzoic acid, salicylic acid, aminosalicylic acid, acetic anhydride, butyric anhydride, valeric anhydride, lauric anhydride, glycine anhydride, crotonic anhydride and the like.

As exemplary species of the dicarboxylic acids and anhydrides thereof, there may be mentioned oxalic acid, succinic acid, tartaric acid, glutaric acid, fumaric acid, maleic acid, malonic acid, citraconic acid, itaconic acid, (o—, m—, p—) phthalic acid, ($\alpha,\beta$—) naphthalic acid, 2,3-naphthalenedicarboxylic acid, 2-methacryloyloxyethyl trimellitate, succinic anhydride, maleic anhydride, citraconic anhydride, itaconic anhydride, phthalic anhydride, naphthalic anhydride, 1,8-naphthalenedicarboxylic anhydride, 2-methacryloyloxyethyl trimellitic anhydride, and the like.

Among the tricarboxylic acids and anhydrides thereof are citric acid, trimellitic acid, trimesic acid, and trimellitic anhydride.

Among said tetracarboxylic acids and anhydrides thereof are ethylenediaminetetracetic acid (EDTA), salts thereof, pyromellitic acid, and pyromellitic anhydride. Poly(meth)acrylic acid can also be useful.

Further, the organic carboxylic acids may contain acid salts as a part of the organic acids. The salts of said organic carboxylic acids are not necessarily limited as long as the counterion does not interfere with the desired effect. Examples of such cations are alkali metal ions and organic cationic species (including tertiary lower alkyl amines and ammonium).

These organic carboxylic acids may be used alone or in combination. Particularly preferred species of such organic carboxylic acids are citric acid, succinic acid, oxalic acid, tartaric acid and ethylenediaminetetracetic acid, salts thereof, maleic anhydride and succinic anhydride.

The concentration of such organic carboxylic acid in the ternary dental composition consisting of organic carboxylic acid, metal chloride and water may range from 5 to 50 percent by weight and is preferably 5 to 30 percent by weight. In the case of citric acid, the range of 5 to 30% by weight is preferable. Outside of the above range, the etching effect will not be sufficient.

The metal chloride which can be incorporated in the ternary composition of this invention is potassium chloride, calcium chloride or a mixture thereof and the concentration of such metal chloride in the total composition may range from 5 to 50 percent by weight. Particularly beneficial is calcium chloride in the concentration range of 5 to 30 percent by weight.

Kojima et al (Journal of the Japanese Society for Dental Materials and Devices, 1, 131, 1982) reported the results they obtained by treating the tooth surface with an aqueous solution containing 10 weight percent of citric acid and 3 weight percent of a metal chloride. According to them, when zinc chloride was used as the metal chloride, the bond strenght with respect to the dentin was not more than 44 kg/cm$^2$, which is insufficient for a bonding agent.

Further, ferric chloride provided a high bond strength with respect to the dentin but because the tooth surface was discolored brown on adsorption of iron ion, this metal salt was undesirable from an aesthetic point of view. However, it is surprising that the dental composition of this invention, despite the fact that it contains a metal chloride in high concentration, does not cause discoloration of the dentin but produces a marked improvement in the adhering effect without detracting from the aesthetic quality of the tooth. However, if the concentration of the metal chloride exceeds 50 percent by weight, there may not be obtained a satisfactory etching effect.

In the dental composition of this invention, there may be incorporated, as desired, a thixotropic agent or rheology modifier so that the composition is fluid during application to the tooth surface, and it will rapidly lose fluidity after application i.e., thixotropy, thus enabling topical application. The composition may be colored with an edible coloring agent for assisting in the identification of the application site. Examples of said thixotropic agent include high molecular weight thickeners such as polyvinylpyrrolidone, carboxymethylcellulose, highly dispersible silica such as fumed silica, and the like. Examples of said edible coloring agent include various food colorants which are commonly used in food and pharmaceutical industries.

The invention now being generally described, the same will be better understood by reference to the following examples, which are not intended to limit the present invention in any manner, unless so stated.

EXAMPLES 1 to 16

In accordance with the formulas given in Table 1, dental compositions were prepared using various organic carboxylic acids and metal chlorides. Each of these test compositions was prepared by charging a 100 ml beaker with the specified quantities of organic carboxylic acid and water and, then, with the specified quantity of metal chloride and stirring the contents thoroughly until a clear fluid was obtained. In a like manner, control compositions were prepared in accordance with the formulas also given in Table 1. After the tooth was treated with each treating agent, a dental composite resin was applied to the tooth and the bond strenght between the composite resin and the tooth was measured by the following procedure for evaluating the effect of the test composition.

BOND STRENGTH TEST

The labial surface of a fresh bovine foretooth which had been preserved frozen immediately after extraction was buffed with silicon carbide paper to prepare a smooth enamel or dentin surface. Then, a spacer provided with an aperture having a specified area was placed on the polished surface.

The test composition preadjusted to the specified concentration was applied to the above enamel or dentin surface in the aperture and allowed to stand for 40 seconds. The tooth was rinsed and dried in an air current. The treated enamel or dentin surface was then coated with bonding containing phosphate monomer (Cleafil ® Photo Bond, Kuraray Co., Ltd.) and allowed to stand for 30 seconds. The volatile substance was evaporated off in an air current, and using a light irradiator (Quick Light, J. Morita Corporation), the bonding agent was photopolymerized for 20 seconds.

A dental composition resin (Cleafil ® Photo Posterior, Kuraray Co., Ltd.) was placed on the above suface. Then, the resin was cured by exposure to said irradiator for 60 seconds. The spacer was removed and a stainless steel bar was rigidly secured to the cured composite resin with a dental cement containing phosphate monomer (Panavia ®, Kuraray Co., Ltd.). The tooth was allowed to stand in water at 37° C. for 24 hours, after which the tensile bond strength was measured using a universal tensile tester at a pulling speed of 2 mm/minute. Thus, it was assured that there would not be a failure between the cured composite resin and the stainless steel bar.

EFFECT OF TREATMENT

The dental composition of this invention produced an improved bond between the dental composite resin and the tooth. In contrast, the reference control compositions provided for a sufficient bond strength with respect to the enamel but only an inadequate bond to the dentin. Furthermore, an electron microscopic comparison of Example 5 with Control Example 2 showed that Example 5 caused less denaturation damage to collagen fiber of bovine tooth pulp.

TABLE 1

| | Acid | | Metal chloride | | Bond strength (kg/cm$^2$) | |
|---|---|---|---|---|---|---|
| | Kind | Weight % | Kind | Weight % | Enamel | Dentin |
| Example 1 | Citric acid | 5 | CaCl$_2$ | 5 | 104 | 102 |
| Example 2 | Citric acid | 5 | CaCl$_2$ | 50 | 176 | 80 |
| Example 3 | Citric acid | 10 | CaCl$_2$ | 5 | 186 | 103 |
| Example 4 | Citric acid | 10 | CaCl$_2$ | 10 | 160 | 97 |
| Example 5 | Citric acid | 10 | CaCl$_2$ | 20 | 199 | 110 |
| Example 6 | Citric acid | 10 | CaCl$_2$ | 40 | 188 | 81 |
| Example 7 | Citric acid | 20 | CaCl$_2$ | 20 | 193 | 120 |
| Example 8 | Citric acid | 20 | CaCl$_2$ | 30 | 173 | 127 |
| Example 9 | Citric acid | 50 | CaCl$_2$ | 5 | 186 | 102 |
| Example 10 | Citric acid | 10 | KCl | 20 | 185 | 92 |
| Example 11 | Succinic acid | 5 | CaCl$_2$ | 10 | 106 | 90 |
| Example 12 | EDTA.2Na | 15 | CaCl$_2$ | 20 | 129 | 99 |
| Example 13 | Tartaric acid | 10 | CaCl$_2$ | 20 | 157 | 83 |
| Example 14 | Oxalic acid | 10 | KCl | 20 | 128 | 87 |
| Example 15 | Maleic anhydride | 10 | CaCl$_2$ | 20 | 135 | 96 |
| Example 16 | Succinic anhydride | 10 | CaCl$_2$ | 20 | 124 | 85 |
| Control Example 1 | Phosphoric acid | 40 | — | — | 204 | 71 |
| Control Example 2 | Phosphoric acid | 50 | FeCl$_3$ | 20 | 180 | 69 |
| Control Example 3 | Citric acid | 10 | — | — | 144 | 70 |
| Control Example 4 | Citric acid | 10 | FeCl$_3$ | 3 | 140 | 74 |
| Control Example 5 | EDTA.2Na | 15 | — | — | 98 | 79 |

It is apparent from the above results that the present invention provides a dental composition which can simultaneously treat both the enamel and the dentin effectively.

What is claimed as new and desired to be secured by Letters Patent of the United States is:

1. A dental composition for the treatment of the enamel or dentin of a tooth comprising an organic carboxylic acid or an anhydride thereof, a metal chloride and water, the concentration of said organic carboxylic acid or anhydride thereof being 5 to 50 weight percent based on the total weight of said composition, said metal chlorine being potassium chloride or calcium chloride or a mixture thereof and the concentration of said metal chloride being 5 to 50 weight percent based on the total weight of said composition.

2. The dental composition of claim 1, wherein said organic carboxylic acid is selected from the group consisting of citric acid, succinic acid, oxalic acid, tartaric acid and ethylenediaminetetracetic acid, or a salt of said ethylenediaminetetracetic acid.

3. The dental composition of claim 1, wherein said organic carboxylic acid anhydride is selected from the group consisting of maleic anhydride and succinic anhydride.

4. The dental composition of claim 1, wherein each of citric acid and calcium chloride is contained in a concentration of 5 to 30 weight percent based on the total weight of the composition.

5. The dental composition according to claim 1, which further comprises a thixotropic agent selected from the group consisting of high molecular weight thickeners of polyvinylpyrrolidone and carboxymethylcellulose, and a highly-dispersable silica.

* * * * *